United States Patent [19]

Kruper et al.

[11] Patent Number: 5,371,303
[45] Date of Patent: Dec. 6, 1994

[54] ONE-STEP PREPARATION OF 4,6-DINITRORESORCINOL FROM RESORCINOL

[75] Inventors: William J. Kruper, Sanford; Zenon Lysenko, Midland; John W. Hull, Jr., Midland; George J. Frycek, Midland, all of Mich.

[73] Assignee: The Dow Chemical Company, Midland, Mich.

[21] Appl. No.: 213,767

[22] Filed: Mar. 16, 1994

[51] Int. Cl.$^5$ .................. C07C 205/23; C07C 205/20
[52] U.S. Cl. ...................................... 568/711; 568/710
[58] Field of Search ........................... 568/710, 711

[56] References Cited

U.S. PATENT DOCUMENTS

| | | | |
|---|---|---|---|
| 3,694,513 | 9/1972 | Tobey et al. | 568/711 |
| 3,715,384 | 2/1973 | Pianka et al. | 568/711 |
| 4,533,692 | 8/1985 | Wolfe et al. | 524/417 |
| 4,745,232 | 5/1988 | Schmidt et al. | 568/711 |
| 4,982,001 | 1/1991 | Lysenko et al. | 564/418 |

FOREIGN PATENT DOCUMENTS

| | | | |
|---|---|---|---|
| 154535 | 10/1963 | U.S.S.R. | 568/711 |
| 1060613 | 12/1983 | U.S.S.R. | 568/711 |

OTHER PUBLICATIONS

*Synthesis of 4,6–Dinitroresorcinol* by Robert J. Schmitt et al. listed in *J. Org. Chem. 1988*, 53, pp. 5568–5569; ©1988 American Chemical Society.

*2,4,6–Trinitroresorcinol* by B. A. Bydal, on *Organic Preparations and Procedures Int.* 5(6), 271–72 (1973) ©1973 by Organic Preparations and Procedures, Inc.

*Dinitroso–Resorcinol* by W. R. Orndorff et al. listed in vol. 45 pp. 1536–1539.

*Primary Examiner*—Werren B. Lone

[57] ABSTRACT

4,6-Dinitroresorcinol is prepared by reacting resorcinol with concentrated nitric acid that is substantially free of suboxides of nitric acid. It has been found that greater than 60 percent yields of the desired product can be obtained when the concentration of aqueous nitric acid used is between about 80 and about 93 weight percent, and the concentration of suboxides is less than about 2 weight percent based on the weight of nitric acid.

10 Claims, No Drawings

ONE-STEP PREPARATION OF 4,6-DINITRORESORCINOL FROM RESORCINOL

BACKGROUND OF THE INVENTION

This invention relates to a process for preparing 4,6-dinitroresorcinol in one step from resorcinol.

4,6-Dinitroresorcinol is used to prepare 4,6-diaminoresorcinol, which is a precursor to polybenzoxazoles (PBOs), polymers which are useful as insulators, solar arrays, and cut-resistant gloves. PBOs can be prepared by reacting 4,6-diaminoresorcinol with bisacids, bisacid halides, bisesters, bisamides, or bisnitriles. See Wolfe in Mark et al., *The Encyclopedia of Polymer Science and Engineering*, Volume 11, pp. 601–635, Wiley-InterScience Publication, New York, 1988.

Efforts to prepare 4,6-dinitroresorcinol in one step from resorcinol and nitric acid in yields exceeding 30 percent have been unsuccessful due to the formation of high levels of undesirable by-products, such as 2,4-dinitroresorcinol and 2,4,6-trinitroresorcinol (styphnic acid). Improved yields of the desired 4,6-isomer have been obtained by introducing bulky protecting groups at the 1- and 3-positions of resorcinol, thereby inhibiting nitration at the 2-position. For example, Lysenko et al. (U.S. Pat. No. 4,982,001, herein incorporated by reference) describes the preparation of 4,6-dinitroresorcinol from resorcinol through a 1,3-bis(methylcarbonato)benzene intermediate. Similarly, Schmitt et al. (*J. Org. Chem.* 1988, 53, 5568, herein incorporated by reference) describes the preparation of 4,6-dinitroresorcinol in 44 to 66 percent yield from resorcinol diacetate. The steric hindrance of these intermediates causes nitration to take place mostly at the 4- and 6-positions, so that the desired 4,6-diaminoresorcinol can be prepared upon hydrolysis and hydrogenation. Unfortunately, a significant degree of undesirable nitration still occurs at the 2-position of the intermediate, and there is the danger of forming the potentially explosive styphnic acid.

It would be desirable to prepare 4,6-dinitroresorcinol in high yields and at high concentrations in one step from resorcinol without requiring any intermediate protected species.

SUMMARY OF INVENTION

The present invention is a method of preparing 4,6-dinitroresorcinol comprising reacting resorcinol with concentrated nitric acid in the substantial absence of suboxides of nitric acid.

The present invention addresses the deficiencies in the art by preparing 4,6-dinitroresorcinol in one step from resorcinol in greater than 60 percent yields.

DETAILED DESCRIPTION OF INVENTION

The present invention is a method of preparing 4,6-dinitroresorcinol comprising reacting resorcinol with concentrated nitric acid in the substantial absence of suboxides of nitric acid. Under these conditions, it has surprisingly been discovered that 4,6-dinitroresorcinol can be prepared in one step from resorcinol in higher yields and with higher selectivity than previously known one-step nitrations.

The concentrated nitric acid is an aqueous solution that contains from about 80 weight percent, more preferably from about 85 weight percent, and most preferably from about 89 weight percent, to about 93 weight percent, more preferably about 92 weight percent, and most preferably about 91 weight percent nitric acid. In order for the nitration of resorcinol to be carried out in the substantial absence of suboxides of nitric acid (i.e., nitrogen species that have an oxidation state lower than that of nitric acid), it is essential that the concentrated nitric acid be substantially free of suboxides of nitric acid. More particularly, the concentrated nitric acid is substantially free of suboxides that are capable of forming nitrosonium ($NO^+$) ions. Examples of suboxides that are substantially absent in the concentrated nitric acid include nitrogen(IV) species, such as $NO_2$ and $N_2O_4$; and nitrogen(III) species, such as $N_2O_3$ and $HNO_2$. "Substantially free" means that the reaction mixture, more particularly the concentrated nitric acid, contains less than 2 weight percent, preferably less than 1 weight percent, more preferably less than 0.5 weight percent, and most preferably less than 0.1 weight percent of suboxides of nitric acid based on the weight of nitric acid. The levels of suboxides of nitric acid can be determined by titration with, for example, hydrogen peroxide. Selectivity and yield of the desired 4,6-dinitroresorcinol is improved at the preferred, more preferred, and most preferred concentrations of nitric acid and suboxides of nitric acid.

Concentrated nitric acid that is substantially free of suboxides of nitric acid can be prepared by known methods, including, for example, first combining a less concentrated nitric acid (i.e., less than about 80 weight percent aqueous nitric acid) with a dehydrating reagent, such as sulfuric acid, then distilling the nitric acid, preferably at reduced pressure, to form about 100 weight percent nitric acid. The desired concentration of nitric acid can then be prepared by adding water, preferably distilled water, to the distilled nitric acid.

Alternatively, the concentrated nitric acid that is substantially free of suboxides of nitric acid can be prepared by first adding a sufficient amount of a peroxide, preferably hydrogen peroxide, to greater than about 90 weight percent, more preferably greater than about 95 weight percent nitric acid, to oxidize any suboxides of nitric acid to nitric acid, then adding sufficient water to achieve the desired concentration of nitric acid.

In general, less concentrated nitric acid inherently contains lower levels of suboxides of nitric acid than the more concentrated nitric acid. This is because the less concentrated nitric acid is more stable to suboxide formation than the more concentrated nitric acid. Therefore, the preferred preparation of concentrated nitric acid that is substantially free of suboxides of nitric acid depends on the initial concentration of nitric acid that is being purified. Lower initial concentrations tend to require a dehydrating reagent, whereas higher initial concentrations tend to require an oxidizing reagent, or perhaps a combination of an oxidizing reagent and a dehydrating reagent.

It is most preferable to prepare concentrated nitric acid that is substantially free of suboxides of nitric acid by adding a sufficient amount of hydrogen peroxide to greater than about 95 weight percent nitric acid to oxidize any suboxides of nitric acid to nitric acid, then adding sufficient water to achieve the desired concentration of nitric acid.

Surprisingly high initial concentrations of resorcinol can be used in this reaction without negatively affecting the product yields. The initial concentration of resorcinol ranges preferably from about 1 weight percent, more preferably from about 5 weight percent, and most preferably from about 10 weight percent, to about 18 weight percent, more preferably to about 16 weight percent, and most preferably to about 14 weight percent, based on the weight of resorcinol and the weight of pure nitric acid in the concentrated nitric acid medium. Higher throughput can be obtained at the most preferred initial concentrations of resorcinol without sacrificing product yield.

The nitration of resorcinol is carried out at subambient temperatures, preferably from about 0° C., more preferably from about −5° C., and most preferably from about −15° C., to about −50° C., more preferably to about −35° C., and most preferably to about −25° C. It is also preferred that resorcinol be added to a stoichiometric excess of the nitric acid, more preferably at least about a 5-fold stoichiometric excess (i.e., at least about 10 moles of nitric acid per mole of resorcinol), and at such rate to control the resulting exotherm. Though the resorcinol is preferably added to the concentrated nitric acid in the absence of a solvent, solvent exclusion is not essential. For example, the resorcinol may be first dissolved in preferably a minimal amount of about 50 weight percent to about 70 weight percent aqueous nitric acid that is substantially free of suboxides of nitric acid, to form a resorcinol/aqueous nitric acid solution that is relatively stable to nitration. This solution can then be added to the concentrated nitric acid under the reaction conditions described above.

It is preferred that the reaction be allowed to proceed to substantial completion, as determined, for example, by the substantial absence of 4-nitroresorcinol in the product mixture, more preferably when the product contains less than 1 weight percent 4-nitroresorcinol based on the ideal yield of the desired product. To this end, the reaction is advantageously monitored by HPLC. The selectivity and yield of 4,6-dinitroresorcinol are improved at the preferred, more preferred, and most preferred temperature ranges, as well as the most preferred mode of addition.

The reaction can be quenched with sufficient water to inhibit further nitration. The product is a mixture predominantly of 4,6-dinitroresorcinol and 2,4-dinitroresorcinol. The overall selectivity for 4,6- and 2,4-dinitroresorcinol is generally found to exceed 90 weight percent, and the overall selectivity for 4-nitroresorcinol and styphnic acid is generally found to be less than 2 percent when the most preferred conditions are used. Furthermore, the ratio of 4,6-dinitroresorcinol to 2,4-dinitroresorcinol in the final product is generally found to be greater than 2:1, and the yield of the 4,6-dinitroresorcinol is generally greater than 60 percent when the most preferred conditions are used.

The desired 4,6-isomer can easily be separated from the 2,4-isomer, due to the marked differences in the solubility of the two isomers in various solvents. For example, the 4,6-isomer can be isolated in about 99 weight percent purity by recrystallization in a suitable solvent, such as acetic acid.

The 4,6-dinitroresorcinol can be reduced to 4,6-diaminoresorcinol by known methods (see Lysenko, supra). The 4,6-diaminoresorcinol can then be reacted with bisacids, bisacid halides, bisesters, Bisamides, or bisnitriles to form polybisbenzoxazoles (PBOs), polymers which are useful as insulators, solar arrays, and cut-resistant gloves. (See Wolfe, supra.)

The invention disclosed herein suitably may be practiced in the absence of any component not specifically disclosed herein.

The following example is provided to illustrate the invention, but is not intended to limit the scope thereof. All parts and percentages are by weight unless otherwise indicated.

EXAMPLE 1

To a solution of 111 g of 90 percent nitric acid (diluted from 100 percent distilled nitric acid that contains less than 0.1 weight percent suboxides of nitric acid) in a 250 mL 3-necked round-bottom flask is added granular resorcinol (13.0 g, 118 mmol, 13 weight percent based on the weight of pure nitric acid) over a 1.3 hour period. The solution is stirred vigorously and the reaction temperature is maintained between about −21° C. and about −15° C. After the addition of resorcinol is complete, the reaction is stirred until less than 1 percent of 4-nitroresorcinol remains in the reaction mixture (about 15 minutes), as monitored by HPLC. The reaction is then quenched with 100 mL of water, while the temperature is maintained at below −5° C. for 15 minutes. The resultant slurry is filtered and the orange yellow solid is washed with 40 mL of water. The solid is then dried to constant weight in vacuo to afford 19.65 g of a 72:28 mixture of a 4,6-dinitroresorcinol to 2,4-dinitroresorcinol. Quantitative assay of the composite reaction mixture (the dried solid and the mother liquor) by an external standard HPLC method is 1.0 percent styphnic acid, 0.78 percent 4-nitroresorcinol, 30.8 percent 2,4-dinitroresorcinol, and 60 percent 4,6-dinitroresorcinol. This dried material was recrystallized from 140 g of hot acetic acid to give yellow crystalline 4,6-dinitroresorcinol which assayed at 98.91 percent purity (0.54 percent 2,4-dinitroresorcinol). The isolated yield is 54 percent.

What is claimed is:

1. A method of preparing 4,6-dinitroresorcinol comprising reacting resorcinol with concentrated nitric acid in the substantial absence of suboxides of nitric acid.

2. The method of claim 1 wherein the nitric acid contains less than about 1 weight percent of suboxides of nitric acid based on the weight of the concentrated nitric acid.

3. The method of claim 2 wherein the nitric acid contains less than about 0.5 weight percent of suboxides of nitric acid based on the weight of the concentrated nitric acid.

4. The method of claim 3 wherein the nitric acid contains less than about 0.1 weight percent of suboxides of nitric acid based on the weight of the concentrated nitric acid.

5. The method of claim 4 wherein the concentrated nitric acid contains from about 85 to about 92 weight percent nitric acid.

6. The method of claim 5 wherein the concentrated nitric acid contains from about 89 to about 91 weight percent nitric acid.

7. The method of claim 6 wherein the resorcinol is reacted with the concentrated nitric acid at about −5° C. to about −35° C.

8. The method of claim 7 wherein the resorcinol is reacted with the concentrated nitric acid at about −15° C. to about −25° C.

9. The method of claim 8 wherein the resorcinol is added to the concentrated nitric acid.

10. The method of claim 9 wherein at least 10 weight percent resorcinol based on the weight of pure nitric acid is added to the concentrated nitric acid.

* * * * *